(12) United States Patent
Wang

(10) Patent No.: US 7,448,798 B1
(45) Date of Patent: Nov. 11, 2008

(54) SCANNING THERMAL PROBE MICROSCOPE

(75) Inventor: Chunhai Wang, Sunnyvale, CA (US)

(73) Assignee: Veeco Instruments Inc., Plainview, NY (US)

( * ) Notice: Subject to any disclaimer, the term of this patent is extended or adjusted under 35 U.S.C. 154(b) by 0 days.

(21) Appl. No.: 10/464,379

(22) Filed: Jun. 18, 2003

(51) Int. Cl.
G01K 7/16 (2006.01)
G01K 3/00 (2006.01)
G01K 13/00 (2006.01)
G01N 25/20 (2006.01)

(52) U.S. Cl. .......... 374/183; 374/43; 374/32; 374/163; 702/133; 702/136; 702/130

(58) Field of Classification Search .......... 374/100, 374/137, 163, 164, 179, 185, 44, 45, 57, 374/43, 4, 5, 16, 32; 702/130, 133, 136
See application file for complete search history.

(56) References Cited

U.S. PATENT DOCUMENTS

| | | | |
|---|---|---|---|
| 4,423,967 A * | 1/1984 | Mouton | 374/138 |
| 4,747,698 A * | 5/1988 | Wickramasinghe et al. | 374/6 |
| 5,003,815 A * | 4/1991 | Martin et al. | 374/6 |
| 5,346,306 A | 9/1994 | Reading et al. | 374/10 |
| 5,441,343 A | 8/1995 | Pylkki et al. | 374/44 |
| 5,713,667 A * | 2/1998 | Alvis et al. | 374/178 |
| 5,929,438 A * | 7/1999 | Suzuki et al. | 374/6 |
| 5,969,238 A * | 10/1999 | Fischer | 374/142 |
| 6,095,679 A | 8/2000 | Hammiche et al. | 374/31 |
| 6,200,022 B1 * | 3/2001 | Hammiche et al. | 374/46 |
| 6,487,515 B1 * | 11/2002 | Ghoshal | 374/45 |
| 6,652,139 B2 * | 11/2003 | Cordes et al. | 374/208 |
| 6,692,145 B2 * | 2/2004 | Gianchandani et al. | 374/185 |
| 2002/0110177 A1 * | 8/2002 | Nakayama et al. | 374/44 |

OTHER PUBLICATIONS

Williams et al., "Scanning thermal profiler", Appl. Phys. Lett. 49 (23), Dec. 8, 1986, pp. 1587-1589.

* cited by examiner

Primary Examiner—Edward Lefkowitz
Assistant Examiner—Mirellys Jagan
(74) Attorney, Agent, or Firm—Boyle Fredrickson S.C.

(57) ABSTRACT

An apparatus and method of measuring a parameter associated with a sample is provided. The method includes providing a probe adapted to heat the sample and applying a measuring current having a frequency $\omega_1$ to the probe. In operation, the method measures the amplitude of the voltage across the probe at a frequency $\omega_1$. This amplitude is indicative of a temperature of the probe. The preferred embodiment also provides a method of separating contamination of the thermal data caused by the probe from thermal data associated with the sample under test.

84 Claims, 13 Drawing Sheets

SCANNING THERMAL PROBE MICROSCOPE

BACKGROUND OF THE INVENTION

1. Field of the Invention

The present invention is directed to scanning probe microscopes, and more particularly, a scanning thermal probe microscope employing a thermal probe as both a heat source and a temperature sensor for imaging and sensing thermal properties of a sample.

2. Description of Related Art

Modern materials science is increasingly concerned with the analysis and control of materials at a very small scale. Micro thermal analysis is directed to thermal analysis in conjunction with microscopy techniques using a thermal probe capable of providing thermal excitation. The use of microscopy allows small-scale regions of a sample to be selected for such imaging, for example. Micro thermal analysis is currently being used commercially to characterize various samples such as polymers, biological materials and electronic materials, among other types of samples. Notably, any local disturbance of the structure that results in a change in density, specific heat or thermal conductivity, can be detected by, for example, a thermal probe. One characteristic of particular interest is the glass transition temperature of a polymer, a key parameter in polymer technology. The behavior of a sample around the glass transition temperature is varied from rubbery or viscous to "glassy." Being able to analyze polymers, and particularly their glass transition temperatures, under varying conditions and on a localized state, is of significant interest. Overall, the ability to make measurements such as calorimetric measurements on a localized scale, particularly on the nanometer scale, has been the subject of much development over recent years. The use of the scanning probe microscope has been critical in the development of this technology.

Scanning probe microscopes (SPMs), such as the atomic force microscope (AFM), are devices which typically use a sharp tip and low forces to measure the surface of a sample down to atomic dimensions. Generally, SPMs include a probe having a tip that is introduced to a surface of a sample to detect changes in the characteristics of a sample. By providing relative scanning movement between the tip and the sample, surface characteristic data can be acquired over a particular region of the sample and a corresponding map of the sample can be generated.

In an AFM, for example, in a mode of operation called contact mode, the microscope scans the tip or the sample, while keeping the force of the tip on the surface of the sample generally constant. This is accomplished by moving either the sample or the probe assembly up and down relatively perpendicularly to the surface of the sample in response to a deflection of the cantilever of the probe assembly as it is scanned across the surface. In this way, the data associated with this vertical motion can be stored and then used to construct an image of the sample surface corresponding to the sample characteristic being measured, e.g., surface topography. Similarly, in another preferred mode of AFM operation, known as TappingMode™ (TappingMode™ is a trademark owned by the present assignee), the tip is oscillated at or near a resonant frequency of the associated cantilever of the probe. The amplitude or phase of this oscillation is kept constant during scanning using feedback signals, which are generated in response to tip-sample interaction. As in contact mode, these feedback signals are then collected, stored and used as data to characterize the sample. Note that "SPM" and the acronyms for the specific types of SPMs may be used herein to refer to either the microscope apparatus, or the associated technique, e.g., "atomic force microscopy."

Another type of SPM is the scanning tunneling microscope (STM). In an STM, similar to AFM, a probe having a tip is employed to scan a surface of a sample. However, in STM, the tip is conducting In operation, a current, known as the tunneling current, is made to flow between sample and the free end or apex of tip. This tunneling current is produced in response to a bias voltage applied between the sample and the tip and is sensitive to the tip-sample separation distance. During operation, maintaining a constant tunneling current through the use of the feedback loop thereby gives a generally constant separation of the tip above the sample surface. Similar to AFM, these feedback signals are indicative of a particular characteristic of the sample.

In sum, scanning probe microscopes are widely used for imaging very small objects down to the size of an atom. It provides powerful imaging ability, including sample characteristics relating to physical topography, force, capacitance, static charge and other parameters depending on its mode of use. The science of SPMs has expanded to allow its use for thermal analysis including mapping temperature, thermal conductivity, measurements of phase transition points, etc. One initial attempt to combine SPM and thermal analysis integrated a thermocouple on a metallic tip of the SPM. In this technique, as the tip approaches a sample it is cooled due to the heat transfer between the tip and the sample surface. An acquired temperature signal from the thermocouple is used as the feedback signal to measure, for instance, topography of a material. Since the feedback is used only to maintain the tip temperature constant it does not provide any measure of thermal parameters of the sample surface, it merely provides an alternate way of operating the SPM for non-conducting samples.

Next, in an attempt to measure true thermal parameters of a sample, another technique was developed based on the atomic force microscope, the scanning thermal probe microscope (SthM). In this case, a thermocouple which acts as a temperature sensor is placed at the apex of the AFM cantilever and conventional force feedback of an AFM, as described previously, is used to maintain contact between the tip and the sample. As a result, temperature distribution of a sample can be measured in addition to topography. However, its functions are limited in that it cannot measure thermal properties such as conductivity and phase transitions because it only constitutes a temperature sensor, i.e., it cannot heat a sample.

In yet another attempt to measure more thermal parameters, a scanning thermal probe microscope was developed that employs a resistive probe as both a heat source and a thermometer. Conventional force feedback of an AFM is used. The probe in this case operates at constant temperature while the applied power is monitored. In operation, because the more conductive a sample the more power required to maintain probe temperature, thermal conductivity can be measured by measuring the power used to maintain the probe temperature.

In all of the above-described systems, notably, the system cannot measure thermal properties of a sample that change with temperature. To further extend the capability of SThM, an improved system was developed in which localized thermal analysis was employed using a miniaturized resistive probe (system 20 shown in FIG. 2 and described below). Localized thermal analysis measures thermal properties of material by ramping the temperature of the probe, instead of using constant temperature, from which phase transition points, such as melting points, can be derived.

Turning initially to FIG. 1, a simplified diagram of a prior art resistive probe 20 having a tip 22 includes a resistive heater 24 at its tip which is used for thermal analysis. One example of such a probe is a Wollaston wire based probe (and thus is often referred to as a "Wollaston probe") which, typically, has a coating of silver over a thin core of platinum. At tip 22 of the probe, the silver is etched away exposing the platinum core or filament. With this design, notably, almost all of the electrical resistance of the probe is located at tip 22. As a result, when an electric current is applied to the probe, only the tip heats. In operation, the electrical resistance of the probe also provides a measure of the temperature at the tip.

More particularly, resistive thermal probe 20 consists of three basic parts including a conducting wire 26, a tip 22 and a mirror 28. Tip 22 part has a much larger resistance than conducting wire 26. Mirror 28 is provided to detect the deflection of the probe when the probe interacts with a corresponding sample 30 during operation. Alternatives to the Wollaston probe have been explored by researchers in order to provide better spatial resolution. However, due to the difficulty to integrate a separate thermometer on a tiny tip, these alternatives are typically exclusively resistive probes, which serve as both a heater and a thermometer.

Overall, local thermal analysis is similar to a differential scanning calorimetry or modulated differential scanning calorimetry except it is for a small volume of material. In one known embodiment, DC current is used to raise the probe temperature and AC current is used for thermal modulation. Notably, the AC component of the applied heating input is primarily provided to improve thermal sensitivity, as its rate of change is faster than the DC heating component. This allows a more accurate measurement of power.

Overall, when performing thermal experiments, both components may be desired. Again, the slower DC heating makes it easier for the sample to reach equilibrium when performing the experiment, and the faster AC heating provides better sensitivity for thermal measurements. A schematic diagram of this system is shown in FIG. 2.

FIG. 2 illustrates control and sensing components of a localized thermal analysis instrument 50. Notably, instrument 50 employs two resistive probes 52, 54 to provide the thermal analysis: a reference probe 52 and a sample probe 54. The reference probe 52 is operated in open loop by the combination of a DC current and an AC current provided via a summing circuit 55. The same physical AC current also is applied to the sample probe in open loop. A comparator 56 and an integrator 58 form a feedback loop to maintain the DC voltage over the sample probe 54 following the reference probe 52. The difference between the two DC driving signals (60 and 62), provided by a comparator 64, serves as the circuit's DC output. The difference of AC voltage drops over the two probes is measured by a lock-in amplifier 66, whose amplitude and phase outputs serve as the circuit's AC output.

Using this technique, some phase transitions of materials, such as melting points, can be observed. However, one problem with this technique is that it does not provide reliable data. In particular, the system cannot separate the sample signal from contamination in the data caused by the probe itself. For example, when making polymer measurements, the signal from a probe can be tens of times larger than that from a sample. Despite the introduction of a reference probe and using simple subtraction of the voltages over the sample and reference probes, the problem is not obviated because the probe signal is not eliminated. Primarily, this is due to the fact that the thermal parameters, such as power, temperature, etc. do not have a linear relationship with respect to the measured voltage. As a result, the output is so heavily contaminated that its absolute value (i.e., using the reference probe) provides no useful information concerning the sample. Only abrupt changes in the data may indicate some phase transition in the material and even these signals need to be observed through derivatives of the output signals.

Another drawback of this latter system is that it does not employ a reliable scale of temperature, or provide any control thereof. Because the sample probe is placed on the surface of the sample during the measurement, while the reference probe is not, the sample probe needs to consume more power to keep its temperature following the reference probe. As the two probes are kept at the same voltage, the temperatures are necessarily different, thus injecting errors in the data. Moreover, this difference changes with the conductance of a sample. And, because the signal used to measure the temperature is changing (i.e., the heating current is variable) a true measure of temperature cannot be obtained. In addition, when a small AC current is used for heating, the effective noise associated with the temperature measurement is amplified, causing the data to be unreliable.

As a result, the field of localized thermal analysis was in need of a device that is capable of separating the sample signal from contamination introduced by the measuring probe. Moreover, a system that is able to provide a measure of temperature directly and continuously while in the process of heating the probe is also desired.

SUMMARY OF THE INVENTION

The preferred embodiment overcomes the above-noted drawbacks by providing a scanning thermal probe microscope that separates the sample signal from contamination introduced by the probe itself, thus providing improved range and sensitivity when making thermal measurements. Also, the preferred embodiment measures temperature directly and continuously. This is achieved by using an independent AC current to measure the temperature, a current the amplitude of which is kept constant. As a result, the preferred embodiment is able to operate in a temperature monitoring mode using a selected power input, rather than in a power monitoring mode for a given temperature which as known in the art is difficult to control. In one preferred embodiment, three components of current are provided to operate the thermal probe, a separate high frequency AC current to measure probe temperature, and a low frequency AC current and a DC current to provide a temperature command to heat/cool the sample.

According to a first aspect of the preferred embodiment, a method of measuring a parameter associated with a sample is provided. The method includes providing a probe adapted to heat the sample and applying a measuring current having a frequency $\omega_1$ to the probe. In operation, the method measures an amplitude of the voltage across the probe at frequency $\omega_1$. This amplitude is indicative of a temperature of the probe.

According to another aspect of this preferred embodiment, the method further includes changing the probe temperature based on a command temperature input. Also, preferably, the command temperature input includes a DC voltage that may be provided by a voltage ramp.

In another aspect of this preferred embodiment, the method converts the command temperature input to a drive current and applying the drive current to the probe so as to change the probe temperature. The method also controls the current applied to the probe in response to the measuring step so that the probe temperature is substantially equal to the command temperature input.

In a still further aspect of this preferred embodiment, the command temperature input includes an AC voltage having a frequency, $\omega_2$, that is used to provide temperature or power of the sample.

In another aspect of this embodiment, the method determines an amount of power consumed by the probe and generates a corresponding power signal. And, the method further includes separating contamination caused by the probe from the power signal. Moreover, the separating step includes performing the determining step for both a load condition and a no-load condition. In this case, the method subtracts the no-load power signal from the load power signal at a temperature point to separate the contamination caused by the probe.

According to yet another aspect of this preferred embodiment, the method applies a command power input. Thereafter, AC temperatures for a load condition and a no-load condition are measured. In this case, the method separates the contamination caused by the probe by subtracting the reciprocal of the no-load AC temperature from the reciprocal of the load AC temperature at the power input valve.

In another aspect of this embodiment, the method substantially linearizes the power control mechanism by taking the square root of the command power input.

According to another aspect of this preferred embodiment, $\omega_1$ is a high frequency signal, and $\omega_1$ is greater than $\omega_2$. More preferably, $\omega_1$ is greater than a thermal bandwidth of the probe. Notably, the thermal bandwidth of the preferred resistive probe is about 1 kHz.

According to still another aspect of this preferred embodiment, the method further includes using control feedback to maintain the contact force between the probe and sample constant. The feedback may be indicative of the topography of at least a portion of the sample.

In another feature of the preferred embodiment, a scanning thermal probe microscope includes a probe configured to change a temperature of the sample. An AC current having a frequency, $\omega_1$, is coupled to the probe. Moreover, the microscope measures a probe temperature by measuring a voltage across the probe at frequency $\omega_1$.

According to a further feature of this embodiment, the microscope measures a probe temperature by measuring a voltage across the probe at frequency $\omega_1$. In addition, the microscope further includes a lock-in amplifier for measuring the probe temperature, wherein a reference of the lock-in amplifier is coupled to the AC current.

According to another aspect of this embodiment, the thermal probe microscope further includes a controller that maintains the probe temperature at a setpoint. Preferably, the setpoint is defined by a command temperature input to the controller, and includes at least a DC voltage.

In a further aspect of this preferred embodiment, the command temperature input includes an AC voltage having a frequency, $\omega_2$, that provides temperature modulation of the sample. The thermal probe microscope also includes a computer to determine an amount of power consumed by the probe and to generate a corresponding power signal. Also, the computer separates contamination caused by the probe from the power signal.

More particularly, the thermal probe microscope computes the power for a load condition and a no-load condition and generates corresponding power signals. To separate the contamination caused by the probe, the computer subtracts the no-load power signal from the load power signal at a temperature point.

In a further aspect of this preferred embodiment, included is a separate AC power command having a frequency, $\omega_2$, that provides power modulation of the sample. The thermal probe microscope also includes a computer to determine the temperature response corresponding to the power command. In addition, the computer separates contamination caused by the probe from the temperature signal. More particularly, the thermal probe microscope measures AC temperatures for a load condition and a no-load condition. To separate the contamination caused by the probe, the computer subtracts the reciprocal of the no-load AC temperature from the reciprocal of the load AC temperature at the power input value.

In yet another aspect of this preferred embodiment, the thermal probe of the microscope is a Wollaston wire probe. And, $\omega_1$ is a high frequency signal that is greater than $\omega_2$. Preferably, $\omega_1$ is greater than a thermal bandwidth of the probe, wherein the thermal bandwidth of the probe is about 1 kHz.

In another aspect of the preferred embodiment, a scanning thermal probe microscope includes a probe configured to change a temperature of a sample. An AC temperature measurement current having a frequency, $\omega_1$ is coupled to the probe and a means for measuring a probe temperature using the AC temperature measurement current is also provided.

According to a still further aspect of the preferred embodiment, a method of measuring a parameter associated with a sample with a probe-based instrument includes providing a probe adapted to heat the sample. The method also applies a measuring current having a frequency $\omega_1$ to the probe. A temperature command input is also provided to apply a DC heating current and an AC heating current to the probe, the AC heating current having a frequency $\omega_2$ substantially less than frequency $\omega_1$. In operation, the method measures an amplitude of the voltage across the probe at frequency $\omega_1$. In this case, the amplitude is indicative of a temperature of the probe.

These and other objects, features, and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

A preferred exemplary embodiment of the invention is illustrated in the accompanying drawings in which like reference numerals represent like parts throughout, and in which.

DETAILED DESCRIPTION OF THE PREFERRED EMBODIMENT

The preferred embodiments are directed to a scanning thermal probe microscope for providing thermal analysis using an atomic force microscope. The scanning thermal microscope can image thermal properties of a region of a sample and perform localized thermal analysis at a point of interest. The microscope may combine the ability to obtain a typical AFM image (such as of surface topography) together with thermal images. In this regard, thermal images and typical AFM images may be obtained simultaneously. Depending on experiment criteria, the user typically will select a location of interest for performing local thermal analysis. Notably, with respect to appropriately positioning the probe for performing a localized thermal measurement, a positioning system is required. One such apparatus is shown and described in U.S. Pat. No. 6,530,268, and U.S. Ser. No. 09/803,268, both assigned to the present assignee, the contents of which are hereby expressly incorporated by reference.

Figure 1:
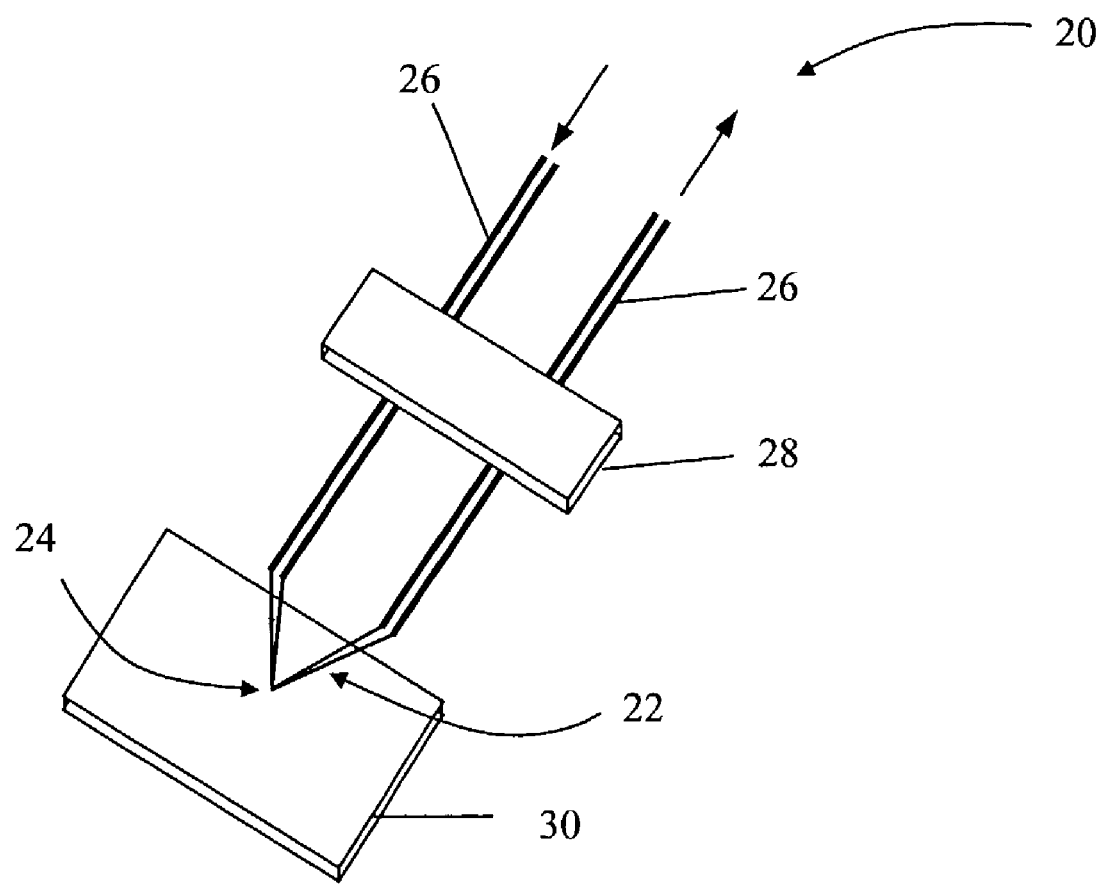
FIG. 1 is a schematic diagram of a prior art resistive probe.
Figure 2:
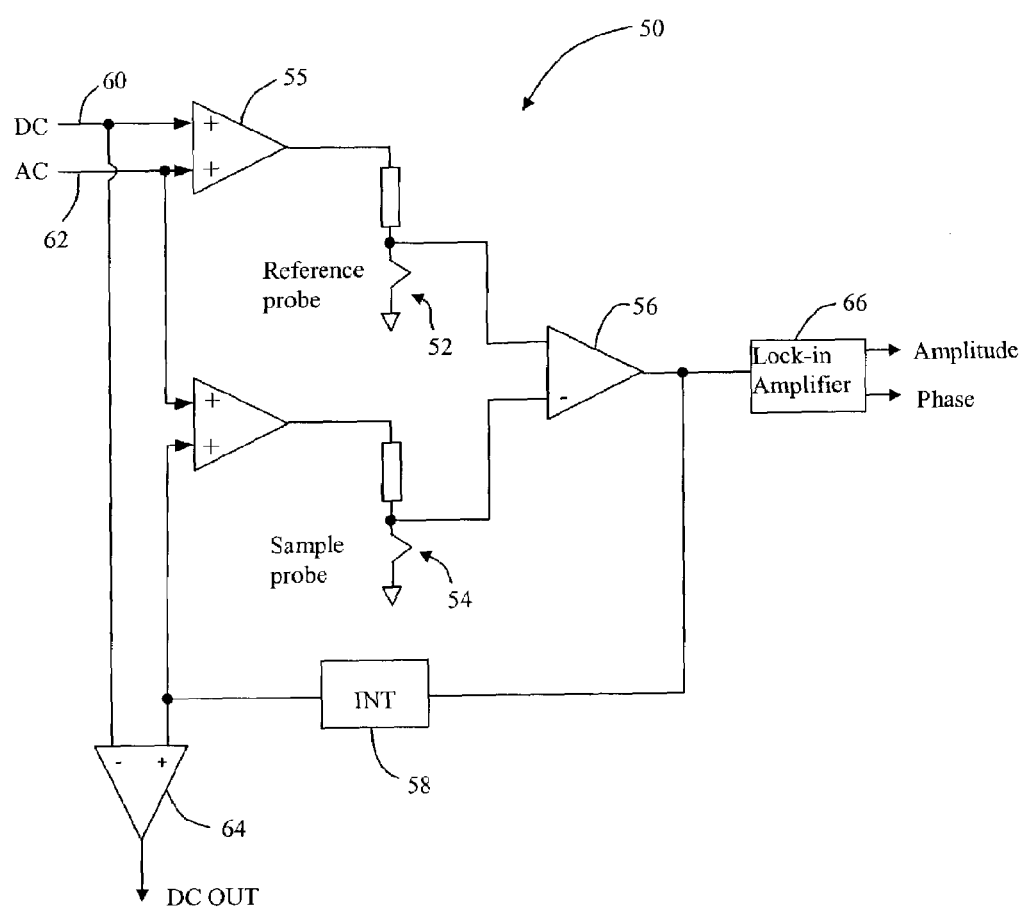
FIG. 2 is a schematic block diagram of a prior art scanning thermal probe microscope employing a resistive probe such as that shown in FIG. 1.
Figure 3:
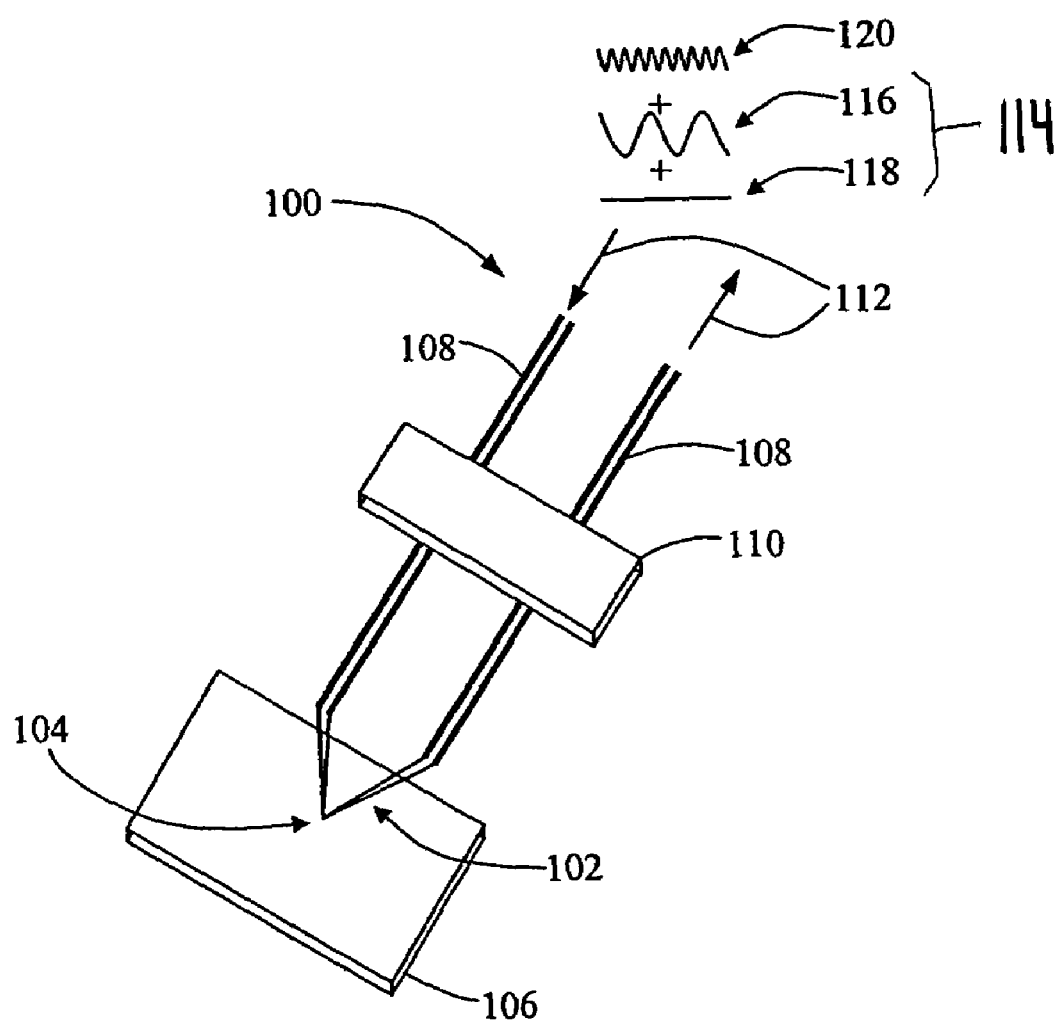
FIG. 3 is a schematic diagram of the resistive probe shown in FIG. 1, illustrating the three input currents that may be applied to the probe in the preferred embodiment.

Turning initially to FIG. 3, the instruments of the preferred embodiments use a resistive probe 100 configured essentially as shown in FIG. 1, described previously. Again, resistive probe 100 has a tip 102 incorporating a resistive heater 104 for thermal analysis of a sample 106.

Notably, the tip of the probe is a very sharp component adapted to also conduct standard AFM measurements. Preferably, the probe is a Wollaston wire probe having a nominal end radius of the tip substantially equal to or less than 10 μm, and preferably less than 2.5 μm. The probe may also be micro-fabricated from silicon, silicon nitride or other similar materials according to known techniques. In the case of a microfabricated probe, a resistive thermal element can be integrated during the manufacturing process or deposited after the fact. Microfabricated silicon based probes can often have a tip having a nominal end radius on the scale of 10 nm. In any case, in the preferred embodiment the probe may be used to make measurements of temperature, sample surface topography, tip/sample force or any combination of the above.

Again, with the probe of FIG. 3, almost all of the electrical resistance of probe 100 is located at tip 102. As a result, when an electrical current is applied to probe 100, only tip 102 changes temperature. The electrical resistance of probe 100 is a measure of the temperature at tip 102. Resistive thermal probe 100 consists of three basic parts including conducting wires 108, tip 102 and a mirror 110. Tip 102 part has much larger resistance than conducting wire 108 so the measured voltage drop across the probe (discussed below) is concentrated on the resistive heater 104. Mirror 110 is used to detect the deflection of probe 100 when the probe interacts with sample 106 during data acquisition. One key difference in the preferred embodiment over the known systems described above is that the present instrument minimizes errors caused by the probe in the acquired thermal data by separating the contributions of the probe 100 from that of the sample 106. Another key is that the electrical current 112 applied to probe 100 includes, in addition to the current used to heat the probe (sometimes referred to herein as the "temperature command"), a high frequency current used exclusively in making temperature measurements.

In fact, the input current 112 to the probe may contain three components, having three associated frequencies as shown in FIG. 3. More particularly, input current 112 includes a temperature command 114 that can be defined by a low frequency component 116 and a DC component 118. In this case, the low frequency component provides periodical heating and cooling of the probe, while the DC current raises probe 100 to the desired temperature. A third current 120 applied to probe 100 is a high frequency component of current that is used to measure the temperature of probe 100, as described below. Ideally, the frequency of temperature measurement current 120 is significantly higher than the thermal bandwidth of probe 100. The thermal bandwidth of the probe can be described as the frequency at which a user can modulate the probe. Typically, for the probes used in the preferred embodiments, this value is about 1 kHz. The frequency of the high frequency modulation of the applied current is set higher than this bandwidth so that the temperature of the probe changes little with the high frequency current.

Figure 4:
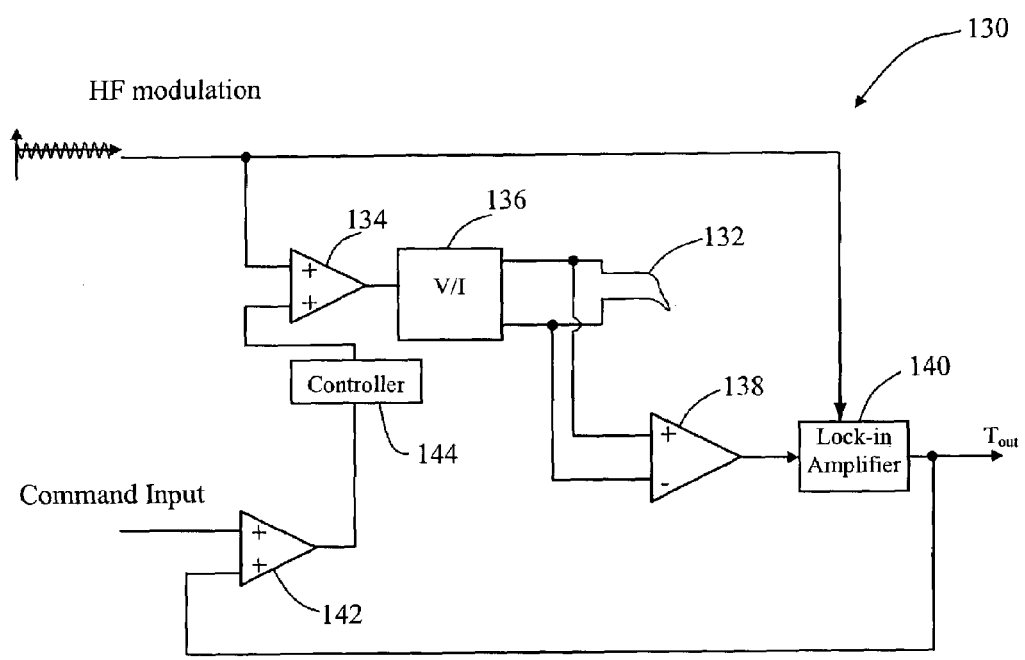
FIG. 4 is a simplified schematic block diagram of a scanning thermal probe microscope according to the present invention.

With reference to FIG. 4, a simplified circuit diagram of a scanning thermal probe microscope 130 according to the present invention is shown. A probe 132, such as that shown in FIG. 3, is driven by a command temperature (labeled "Command T") for thermal measurements. The temperature command signal may simply be a DC voltage ramp or, for instance, a DC voltage ramp modulated with a low frequency AC voltage (FIG. 3) to achieve the benefits of periodical heating, as described above. In addition, a high frequency voltage (labeled "HF modulation") is applied to probe 132 to effectuate temperature measurement, as noted previously and described in detail below.

The high frequency voltage signal (HF modulation) is transmitted to a summing junction 134 to be combined with the command from controller 144. The combination is then transmitted to a voltage/current (V/I) converter 136. Voltage/current converter 136 is a device that generates an output current in response and corresponding to its input voltage, independent of load resistance. The output current from the V/I converter is then applied to probe 132 to appropriately heat/cool probe. Notably, the amplitude of the HF modulation frequency signal is sufficiently small such that its heating effect is negligible.

In operation, a voltage drop over resistive probe 132 when making a thermal measurement is amplified by preamplifier 138, and then is transmitted to a lock-in amplifier 140. Lock-in amplifier (LIA) 140 is a well-known device for measuring an amplitude of a signal-to-be-measured in low noise applications. Typically, an LIA requires two inputs, one to receive a reference signal and the other to receive the signal to-bemeasured which, in this case, is the output of preamplifier 138. Again, the output is the amplified voltage drop across probe 132. Notably, the frequency selectivity of LIA 140 allows only those frequencies approximately equal to the frequency of the reference signal to pass, blocking all other signals. The reference signal in this case is the HF modulation signal.

Figure 5:
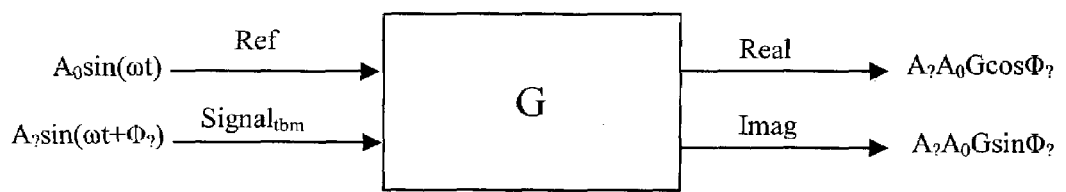
FIG. 5 is a schematic block diagram of a lock-in amplifier, showing the real and imaginary components of its output.

The output signal of LIA 140 includes two components, a real component of the signal and an imaginary component. The real part of the signal provides a measurement of the amplitude of the to-be-measured signal multiplied by the cosine of the phase difference between the two input signals, while the imaginary part of the signal is the amplitude of the to-be-measured signal multiplied by the sine of the phase difference between the two input signals. This is illustrated in FIG. 5. In the case where the phase difference between the two input signals is close to zero, the real part reasonably equals the amplitude of the input signal. In this way, the amplitude of the voltage drop over probe 132 can be determined, from which its resistance or temperature T (labeled "$T_{out}$") can be readily derived.

In the preferred embodiment, closed loop feedback control is used to ensure that the probe is heated according to the temperature command, i.e., the Command T input. In this regard, during operation, the output temperature signal from LIA 140 is fed back to a comparator 142 where it is compared to the Command T signal. Comparator computes the difference between its inputs and generates an output defining a temperature error signal that is applied to a controller 144, such as a proportional integral-differential (PID) controller. Controller 144 applies an appropriate gain to the temperature error signal to compensate for any error between the command temperature and the measured temperature.

Next, the HF modulation is then combined with the output of controller 144 and transmitted to the voltage/current (V/I) converter, as described previously, which generates a current to be applied to the probe 132 to appropriately heat the same. Note that, although the instrument may be operated in open loop (see, for example, FIG. 9, and the corresponding description below), the just-described closed loop configuration has particular advantages. Namely, experimental control can be superior using the closed loop configuration in that measurements can be made at selected precise temperatures with greater certainty given the feedback error compensation.

Note that the signal conditioning electronics have been described using standard analog components. It is understood by those skilled in the art that digital electronics could be readily substituted to provide similar results.

Figure 6:
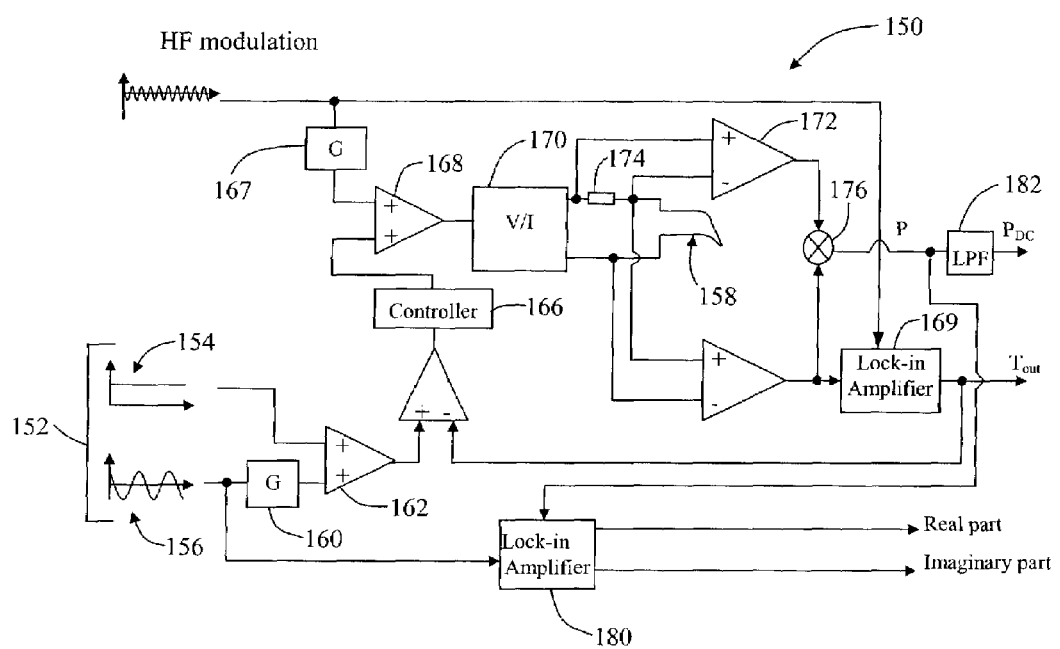
FIG. 6 is a schematic block diagram of the scanning thermal probe microscope of FIG. 4, according to a preferred embodiment.

Next, one implementation of the instrument shown in FIG. 4 is a thermal probe microscope 150 illustrated in FIG. 6. In this case, precise temperature control is provided, while the power can be monitored to determine thermal parameters of a sample. More particularly, thermal parameters are measured by monitoring power consumption for a known DC and AC temperature input. A Command Input 152, a temperature command, includes an input signal 154 as the command signal used to apply DC heating (e.g., a ramp or a step) to probe 158. An AC input signal 156 of temperature command 152 is the low frequency modulation employed to provide periodical heating. Signal 156 is attenuated by attenuator 160. The DC and low frequency signals are combined at summing block 162 and compared with the temperature signal, $T_{out}$, by comparator 164, determined in operation as described above in conjunction with FIG. 4.

The error signal generated by comparator 164 is transmitted to a controller 166. Controller 166 generates a control signal indicative of the desired heating/cooling to be applied to probe 158. This control signal is transmitted to a summing circuit 168 where it combines the high frequency voltage HF modulation. Again, the HF modulation is applied as a separate AC input, which results in a non-changing amplitude of current in the probe, for measuring probe temperature using lock-in amplifier 169 (as described above) during operation. The output of summing circuit 168 is then transmitted to a voltage-to-current converter 170 for generating the current used to drive probe 158. Notably, the electrical current applied to probe 158 is controlled by the value and direction of the error signal. This current causes the temperature of probe 158 to follow the command temperature at the output of summing block 162. In other words, the V/I converter 120 converts the Command Input to a drive current so that the heating power of the probe is substantially proportional to the output of controller 166. Controller 166 can be an integral controller, a PID controller or any other controller that can fulfill this function.

Next, thermal microscope 150 measures the electrical current applied to probe 158 using a preamplifier 172 and a resistor 174 in conventional fashion. Then, using a multiplier 176, this current applied to probe 158 is multiplied by the probe voltage output generated by preamplifier 178, the probe voltage being generated as described in connection with FIG. 4. The output ("P") of multiplier 176 is indicative of the power consumption of probe 158. The power signal P is further transmitted to a second lock-in amplifier (LIA) 180, together with the low frequency AC temperature signal 156 as the reference signal. LIA 180 generates two signals, the real and imaginary parts of the AC power needed to generate the required AC temperature modulation. The combination of the real and imaginary parts of the power forms a complex number that is referred to as the complex AC power hereafter. The power signal P is also transmitted to a low pass filter 182 that generates an output indicative of the DC power needed to generate the required DC temperature. Notably, by changing the attenuation of gain block 160 the AC amplitude of the temperature input can be adjusted, for example, accommodate different types of thermal experiments.

Figure 7:
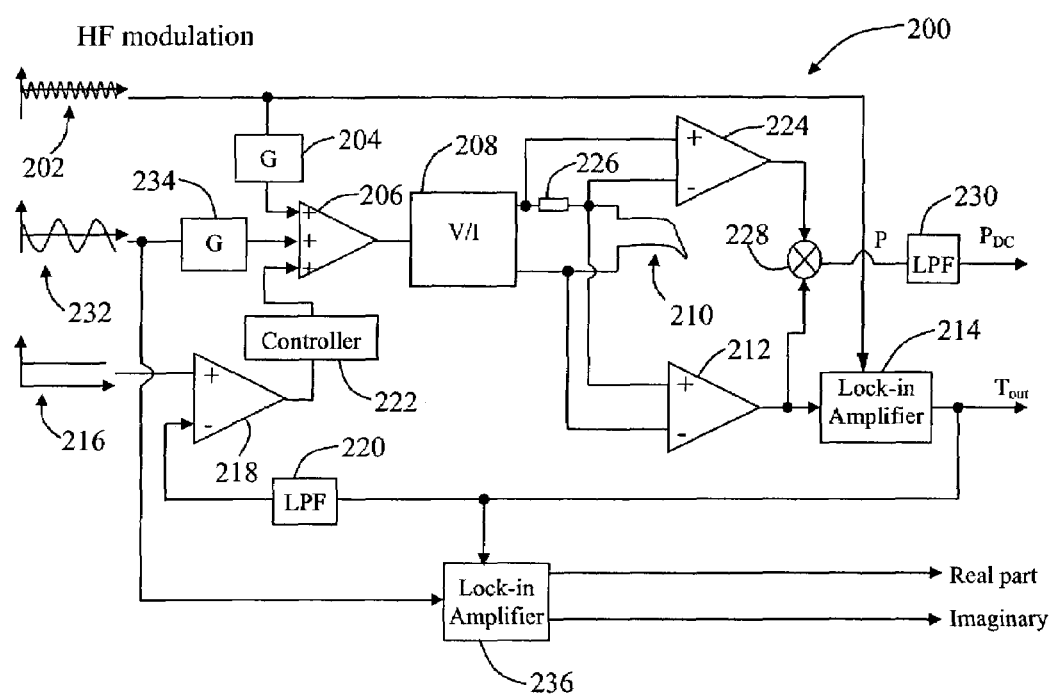
FIG. 7 is a schematic block diagram of a scanning thermal probe microscope of FIG. 4, according to another preferred embodiment.

Turning to FIG. 7, a more preferred embodiment of the microscope is illustrated as instrument 200. In this case, thermal parameters of a sample (not shown) are measured by monitoring DC power consumption for a known DC temperature input, and monitoring AC temperature for a known AC power input. Temperature measurement using a separate high frequency modulation (HF modulation) is as described previously. To review, a high frequency voltage signal 202 is first attenuated by a gain stage 204 prior to being combined with other drive signals (as will be described below) via summing circuit 206. Again, negligible heating of the probe is caused by this high frequency modulation.

The output of summing circuit 206 is transmitted to a voltage/current converter 208 for generating an output current to be applied to a probe 210 to heat the same. The voltage drop over resistive probe 210 is amplified by a preamplifier 212, which transmits its output to a lock-in amplifier (LIA) 214 which has a reference input coupled to the HF modulation signal 202. The amplitude of the output from LIA 214 is proportional to the resistance of probe 210, and thus LIA 214 provides a measure of the temperature of resistive probe 210.

A DC input signal 216 provides a temperature command corresponding to the desired DC temperature. In operation, a comparator 218 compares the DC input signal 216 to the measured DC voltage signal indicative of temperature, obtained after passing temperature signal "$T_{out}$" through a low-pass filter 220. The error signal from comparator 218 is transmitted to a controller 222, which again generates a control signal to produce a current in probe 210 according to the amplitude and direction of the error so as to cause the temperature of probe 210 to follow the desired DC temperature 216. Notably, feedback control, unlike in instrument 150, is used to maintain only the DC component of the temperature command.

As in the previous embodiment, instrument 200 measures the electrical current applied to probe 210 using a preamplifier 224 and a resistor 226 in conventional fashion. A multiplier 228 is provided to multiply the current signal by the probe voltage, as measured by preamplifier 212. As a result, multiplier 228 generates a signal ("P") indicative of the power consumption of the probe to keep the DC temperature following the desired temperature. In particular, the power signal P is transmitted to a low pass filter 230 that generates an output indicative of the DC power needed to generate desired DC temperature.

The AC power input is formed from the low frequency input voltage signal 232 after attenuation by attenuator 234. Signal 232 operates to provide a constant amplitude of current in the probe through voltage/current converter 208. Because the resistance of probe 210 is known, the power is also known (i.e., $P=I^2R$). With this known AC power input, a second lock-in amplifier (LIA) 236 is employed to measure the corresponding AC temperature response. Again, LIA 236 generates two outputs corresponding to the real and imaginary parts of the AC temperature signal. The combination of both parts forms a complex number, which will be referred to as the complex AC temperature.

Notably, changing the attenuation provided by gain stage 234 allows the user to generate varying amplitudes of applied AC power. Also, because power is proportional to the square of all currents passing through probe 210, DC temperature input 216 changes also affect the amplitude of AC power modulation in this design. All current must also be known in order to generate accurate AC power modulation. Overall, instrument 200 may provide an advantage over instrument 150 in FIG. 6 due to the fact that the low frequency AC current modulation may be accomplished more accurately than when using temperature control as described previously, thus improving the sensitivity when making thermal measurements. Moreover, maintaining DC temperature is a more straightforward with respect to implementing controller 222. In contrast, by using feedback to maintain the AC portion of the temperature command, the controller is necessarily more complex, particularly given the greater bandwidth of operation that is required.

Figure 8:
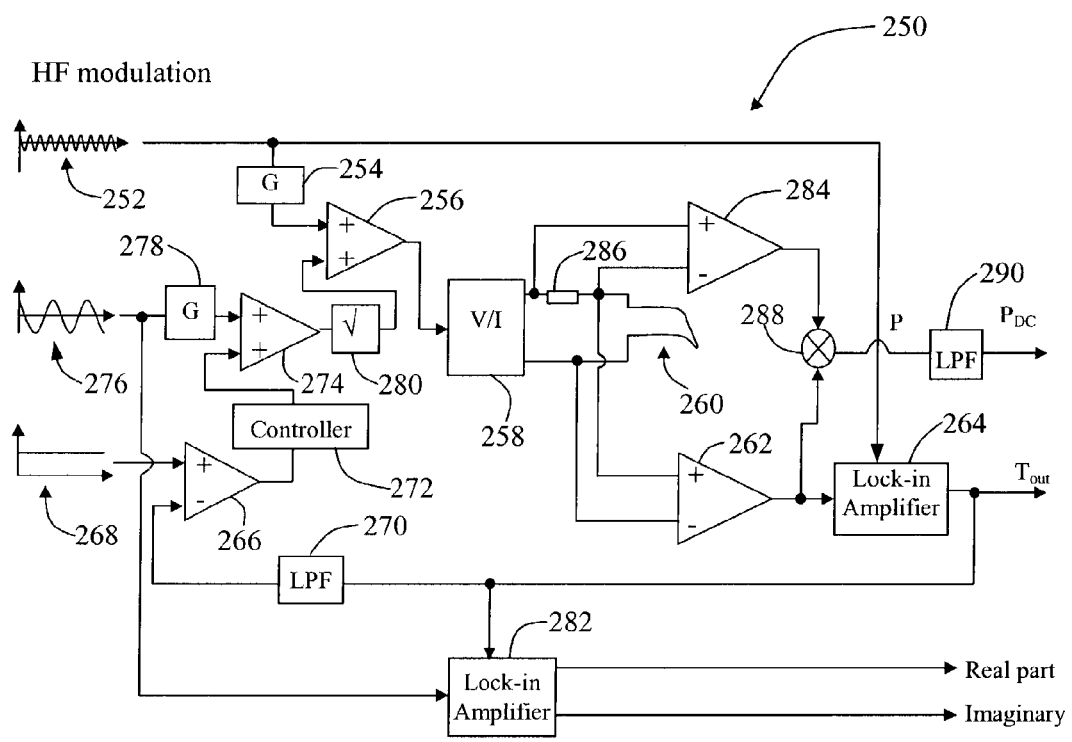
FIG. 8 is a schematic block diagram of a scanning thermal probe microscope of FIG. 4, according to yet another preferred embodiment.

Next, in FIG. 8, an alternative instrument 250 is provided whereby thermal parameters are measured by monitoring DC power consumption for a known DC temperature command input and monitoring AC temperature for a known AC power input. One advantage over FIG. 7 is that it eliminates the influence of DC temperature input on the amplitude of AC power modulation. Very similar to the embodiment shown in FIG. 7, instrument 250 employs a high frequency voltage signal 252 (HF modulation) to measure temperature. An attenuator 254 scales the amplitude of the high frequency modulation to minimize its heating effects, and then transmits its output to a summing circuit 256 for combining with the command signal from square root module 280 prior to transmission to a voltage/current converter 258.

In operation, the instrument measures a voltage drop over resistive probe 260 and amplifies the same with a preamplifier 262. Preamplifier 262 generates a corresponding output signal and transmits that signal to a lock-in amplifier (LIA) 264 as in previous embodiments. The output of LIA 264 is proportional to the resistance of probe 260, and thus the LIA provides signal indicative of the temperature of the resistive probe.

A comparator 266 then compares the DC command temperature 268 to the temperature signal $T_{out}$ after the temperature signal $T_{out}$ is conditioned by a low-pass filter 270. The error signal generated by comparator 266 is then transmitted to a controller 272, which generates a voltage signal that will ultimately be applied to probe 260 as a current, according to the value and direction of the error signal, to cause the DC temperature of the probe to follow the desired DC temperature signal 268. A summing circuit 274 then adds the output command signal of controller 272 with low frequency signal 276 attenuated by attenuator 278. The corresponding output is applied to "square root" electronics 280, prior to being summed with the attenuated high frequency modulation with circuit 256. The output voltage of circuit 256 is then converted to current by V/I converter 258, this current being used to drive probe 260. More particularly, because power is proportional to the square of current, the square root module 280 insures that the AC power modulation of probe 260 does not include a contribution from the DC temperature command 268.

Next, the AC temperature response is measured by a second lock-in amplifier (LIA) 282, which outputs real and imaginary components of the temperature response. Their combination may be referred to as the complex AC temperature. Power signal P, generated using preamplifier 284 and resistor 286 along with multiplier 288 as previously described, is also sent to a low pass filter 290, from which the DC power PDC needed for generating the desired DC temperature is measured.

Figure 9:
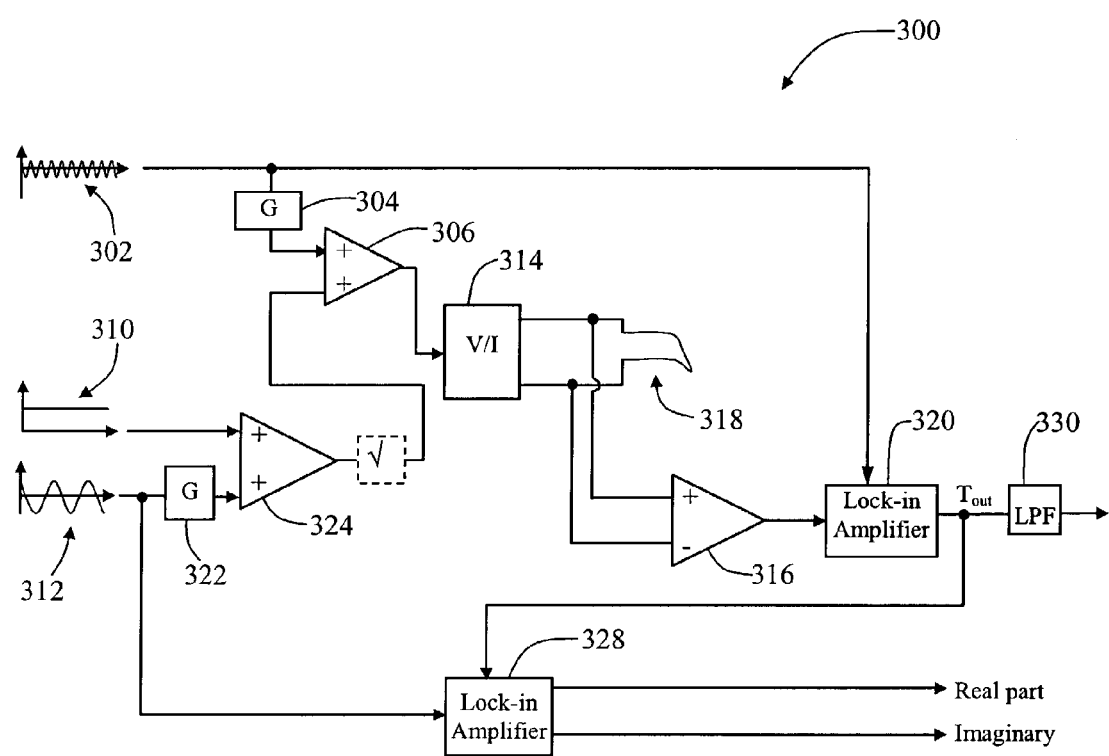
FIG. 9 is a schematic block diagram of a scanning thermal probe microscope of FIG. 4, according to a still further preferred embodiment.

In FIG. 9, thermal parameters of a sample are measured by monitoring the temperature response for known DC and AC power inputs. In this case, contrary to the previously described instruments, thermal probe microscope 300 is operating in open loop. As in each of the previous embodiments, a high frequency voltage signal 302 is employed to measure temperature. The HF modulation 302 is first attenuated by attenuator 304 and then sent to a summing circuit 306 to combine signal originated from power command 308 prior to being transmitted to voltage/current (V/I) converter 314. A preamplifier 316 amplifies the voltage drop over a resistive probe 318 and transmits its output to a lock-in amplifier 320. The output of lock-in amplifier 320 is proportional to the resistance of probe 318, and therefore provides a measure of temperature of resistive probe 318.

A DC input signal 310 represents the desired DC power, which can be implemented as a ramp, a step, etc. The desired AC power is provided with a voltage signal 312, after attenuation by an attenuator 322. Desired DC and AC power signals combine using a summing circuit 324, the output of which may be transmitted to a square root module 326. After being combined with the HF modulation, the drive applied to probe 318 is provided via voltage/current converter 314. In this embodiment, if the square root electronics 326 are employed, the DC and AC power can be independently controlled by the corresponding DC and AC components of the temperature command 308, signals 310 and 312.

Instrument 300 measures the AC temperature response using a lock-in amplifier (LIA) 328, which provides two outputs corresponding to the real and imaginary components of the response, referred to as complex temperature response. The temperature signal T is also applied to a low-pass filter 330, which provides a measure of the DC temperature response corresponding to the DC power input via signal 310. Overall, by using a power input command to ramp measurement conditions, rather than using a temperature command via feedback, higher accuracy in making thermal measurements may be achieved as it is well understood that maintaining a programmed temperature when making thermal measurements can be difficult.

Figure 10A:
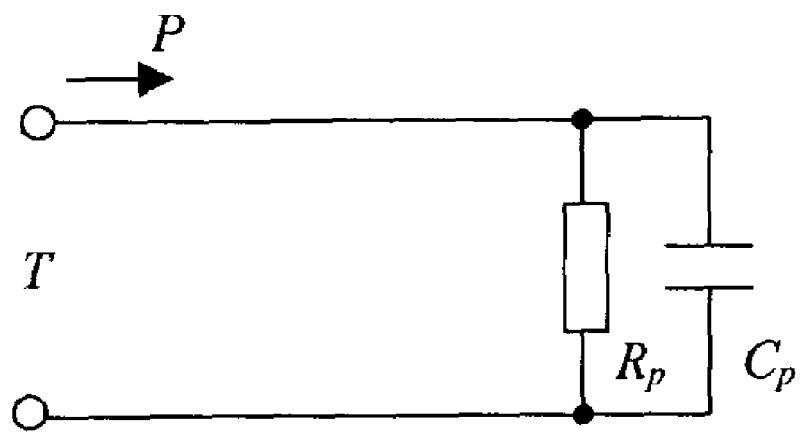
FIG. 10A is a thermal model of the thermal probe, according to a preferred embodiment.

Using the above systems, thermal parameters of a sample, based on the data acquired by these systems, may be plotted. To do so, the probe and sample must be modeled. Note that the following models are only exemplary, and that one skilled in the art will appreciate that alternate models could be substituted with similar results. In FIG. 10A, a thermal model for the probe is provided. The thermal behavior of the probe can be modeled as a thermal resistor $R_p$ in parallel with a thermal capacitor $C_p$. The relation between power consumption P' and temperature increase T follows, $$p' = T/[1/R_p + j\omega C_p] \qquad \text{Equation 1}$$

where $\omega$ is frequency of thermal waves (i.e., the low frequency modulation), and j is the imaginary unit $j = \sqrt{-}$.

Figure 10B:
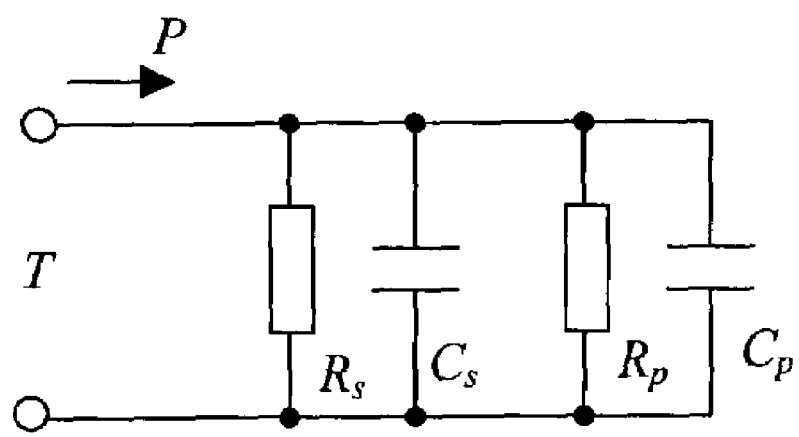
FIG. 10B is a thermal model of the combination of a thermal probe and the sample, according to a preferred embodiment.

In FIG. 10B, a thermal model for both the probe and the sample is shown. Similar to the probe model, the sample being measured can also be described as a thermal resistor $R_s$ in parallel with thermal capacitor $C_s$. During a measurement, the equivalent thermal circuit with the sample plus a probe is shown. The relation between power consumption P and temperature increase T is as follows, $$p = T/[1/R_p + j\omega C_p + 1/R_s + j\omega C_s] \qquad \text{Equation 2}$$

where again $\omega$ is the frequency of the thermal waves (i.e., the low frequency AC modulation).

Figure 11:
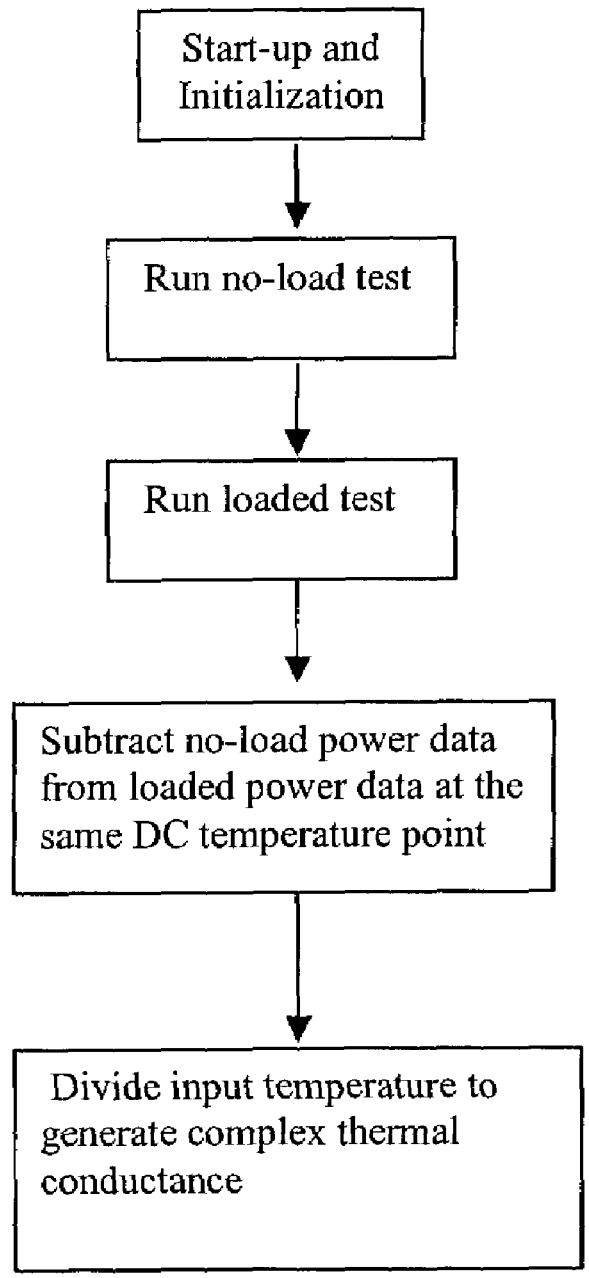
FIG. 11 is a flow chart illustrating operation of the scanning thermal probe microscope of a preferred embodiment in a temperature input mode.
Figure 12:
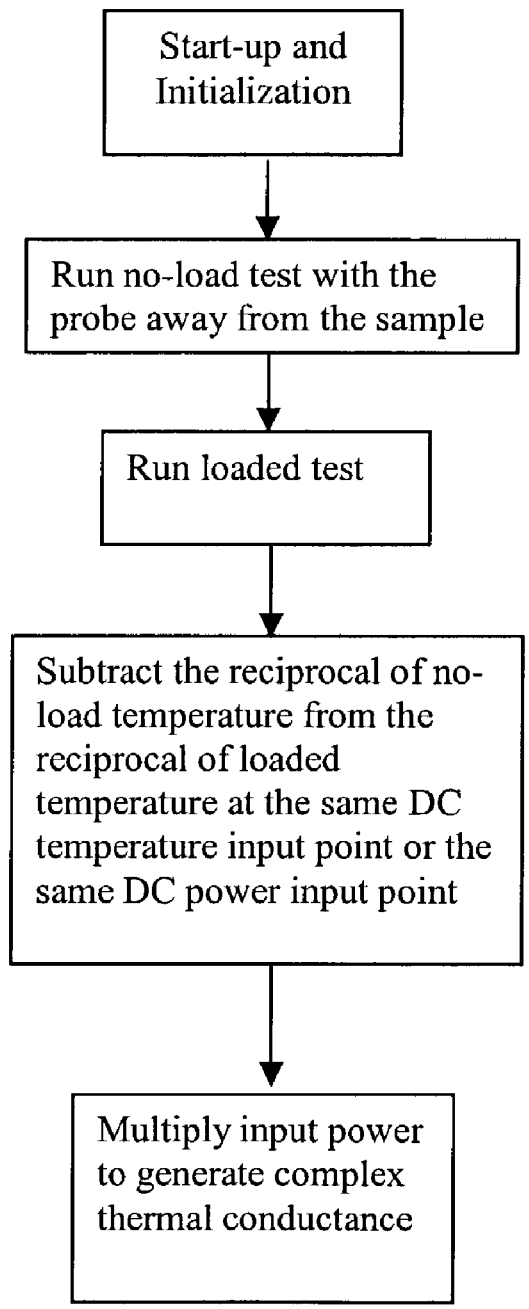
FIG. 12 is a flow chart illustrating operation of the scanning thermal probe microscope of a preferred embodiment in a power input mode.

Using these models, the methods illustrated in FIGS. 11 and 12, together with appropriate embodiments of the scanning thermal probe microscope described above, can be employed to separate thermal information associated with the sample from the contamination to the data caused by the probe. With initial reference to FIG. 11, a method 400 of performing thermal analysis is using a known temperature input ("Temperature Input Mode") includes a start-up and initialization step in Block 402. Then, method 400 performs a no-load measurement where the probe is not in contact with the sample in Block 404. The corresponding data is stored. Then, method 400 runs a normal loaded measurement, in Block 406, where the probe is placed in contact with the sample using the exact same temperature and/or power program (discussed previously) as used in conjunction with the initial no-load measurement in Block 404. In this case, where a known temperature is the input and power is the measured output, the thermal information associated with the probe signal is eliminated by subtracting no-load power from normal loaded power at the corresponding temperature point in Block 408, $$p - p' = T/[1/R_s + j\omega C_s] \qquad \text{Equation 3}$$

wherein p and p' are the power consumption of the probe in normal and no-load measurement respectively. T is the temperature response at corresponding points of both measurements. T can represent either DC or AC temperature. In the case in which T represents DC temperature (FIGS. 6, 7 and 8, for instance), p and p' refer to DC powers at the same temperature point for both measurements. In case T represents AC temperature (FIG. 6, for instance), p and p' refer to AC power consumption at the same DC temperature point for both measurements. Dividing both sides by T in Block 410 yields, $$1/R_s + j\omega C_s = (p - p')/T \qquad \text{Equation 4}$$

which is the complex conductance of the sample at a measured point. Then separating the real and the imaginary parts, $$1/R_s = [\text{real}(p) - \text{real}(p')]/T \qquad \text{Equation 5}$$

and $$\omega C_s = [\text{imag}(p) - \text{imag}(p')]/T \qquad \text{Equation 6}$$

wherein real(p) and real(p') are the real components of the loaded and non-loaded power measurements, imag(p) and imag(p') are the imaginary components of the loaded and non-loaded power measurements. Finally, the thermal conductance can be related to thermal properties of material, $$1/R_s = f(\omega, D, S, \lambda, A) \qquad \text{Equation 7}$$

and $$\omega C_s = g(\omega, D, S, \lambda, A) \qquad \text{Equation 8}$$

where D is the density, S is the specific heat, $\lambda$ is the thermal conductivity and A is the contact area between a probe and a sample. These functions highlight that further interpretation of the real and imaginary parts of complex conductance depend on the model employed, which itself depends on the details of the tip/sample geometry.

Next, with reference to FIG. 12, a method 420 of performing thermal analysis using a known power input ("Power Input Mode") includes a start-up and initialization step in Block 422. Then, method 420 performs a no-load measurement where the probe is not in contact with the sample in Block 424. The corresponding data is stored. Then, method 420 runs a normal measurement, in Block 426, where the probe is placed in contact with the sample using the same settings as used in conjunction with the initial measurement. In this case, power is the known input (FIG. 9, for instance) and temperature is the output. The contribution by the probe to the thermal signal is eliminated by subtracting, as shown in Block 428 the reciprocal of the no-load temperature data from the reciprocal of the normal temperature data, $$1/T - 1/T' = (1/R_s + j\omega C_s)/p \qquad \text{Equation 9}$$

where T and T' represent the temperature response for normal and no-load measurement and p is the power input. Note that p can be either DC or AC power. In the case in which p represents DC power (FIG. 9, for instance), T and T' refer to the DC temperature response at the same power input point for both measurements. In the case in which p represents AC power (FIGS. 7, 8 and 9, for instance), T and T' are indicative of AC temperature response at the same DC temperature input points for both measurements (FIGS. 7, 8), or the same DC power input points (FIG. 9). Multiplying both sides by input power p in Block 430 yields, $$1/R_s + j\omega C_s = p/T - p/T' \qquad \text{Equation 10}$$

which is the complex conductance of the sample at a point corresponding to temperature T. The complex conductance in Equation 10 can also be further interpreted by equation 7 and 8.

Figure 13:
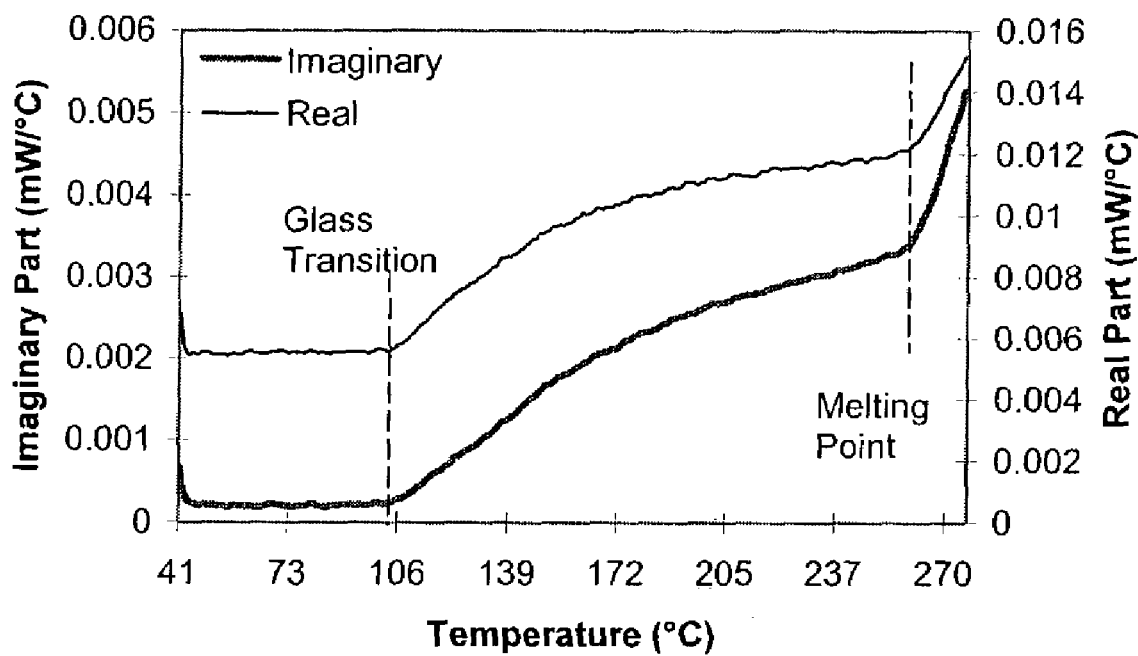
FIG. 13 is graph illustrating the thermal output generated by the present invention when analyzing a Polyethylene Terephthalate (PET) sample.
Figure 14:
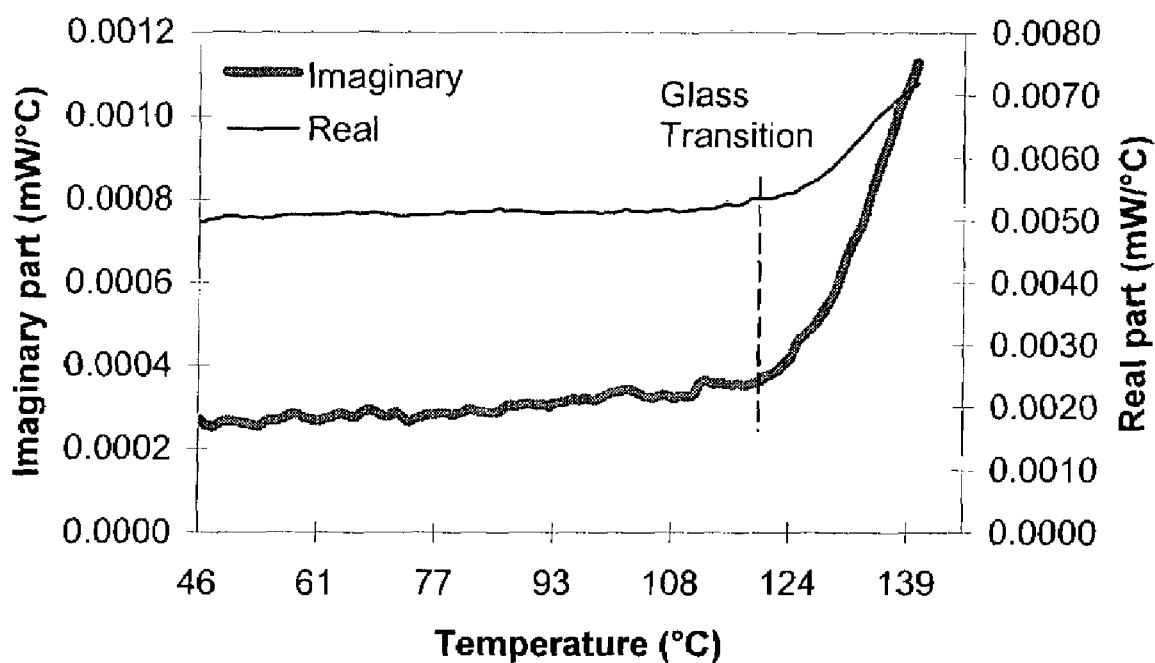
FIG. 14 is a graph illustrating the thermal output generated by the present invention when analyzing a High Impact Polystyrene (HIPS) sample.

FIGS. 13 and 14 illustrate exemplary system output using instrument 250 of FIG. 8. FIG. 13 is a diagram illustrating a practical thermal measurement of PET (Polyethylene Terephthalate). Both the real and imaginary parts of AC conductance are shown in the figure, from which the glass transition, $T_g$, and melting points can be easily identified. More particularly, turning points in the plots, for example, at the points marked "glass transition" and "melting" in FIG. 13, are key indicators of transitions of interest.

FIG. 14 is a diagram illustrating a practical thermal measurement of HIPS (High Impact Polystyrene). Both the real and imaginary parts of AC conductance are shown in the figure, from which transition points of interest can be noted. Again, transitions can often be identified from turning points in the plots. In this example, the glass transition point, $T_g$, can be readily identified.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

What is claimed is:

1. A method of operating a thermal probe microscope to measure a thermal parameter associated with a sample, the method comprising:
providing an electrically resistive probe having a tip;
applying a heating current signal to the electrically resistive probe to heat the sample a selected amount;
applying a measuring current signal having a substantially constant amplitude and having a frequency $\omega_1$ to the electrically resistive probe, wherein the measuring current signal does not substantially heat the sample; and
measuring an amplitude of the voltage across the electrically resistive probe at frequency $\omega_1$, the amplitude being indicative of a temperature of the tip.

2. The method of claim 1, wherein said measuring step includes using a lock-in amplifier.

3. The method of claim 1, wherein the temperature is indicative of the parameter.

4. The method of claim 1, further including the step of:
measuring a power applied to the tip to maintain the temperature of the probe substantially equal to a programmed value.

5. The method of claim 1, wherein the probe is a resistive probe.

6. The method of claim 1, wherein an amplitude of the measuring current is constant.

7. The method of claim 1, further comprising the step of scanning the sample with the probe.

8. The method of claim 1, wherein the probe has a nominal end radius generally less than or equal to 10 μm.

9. The method of claim 8, wherein the nominal end radius is generally less than or equal to 2.5 μm.

10. The method of claim 1, further comprising the step of measuring a signal indicative of a force applied by the probe tip on the sample.

11. The method of claim 10, wherein the force is kept substantially constant using a feedback loop that generates a control signal.

12. The method of claim 10, further comprising the step of changing the force.

13. The method of claim 1, further comprising the step of changing at least one of the probe temperature based on a command temperature input and a probe power based on a command power input.

14. The method of claim 13, further comprising the step of changing both a DC and an AC temperature of the probe.

15. The method of claim 13, wherein the step of changing includes changing both a DC temperature and an AC power of the probe.

16. The method of claim 13, further comprising the step of changing both a DC power and an AC power of the probe.

17. The method of claim 13, wherein an input power is known and the temperature is measured.

18. The method of claim 13, wherein the temperature of the tip is known and a change in the probe power is measured.

19. The method of claim 13, wherein the command power input includes a DC voltage.

20. The method of claim 19, wherein the DC voltage is a ramp.

21. The method of claim 20, further comprising the step of converting the command power input to a drive current so that a heating power of the probe is substantially equal to the command power input.

22. The method of claim 13, wherein the command temperature input includes a DC voltage.

23. The method of claim 22, wherein the DC voltage is a ramp.

24. The method of claim 22, further comprising the steps of converting the command temperature input to a drive current and applying the drive current to change the probe temperature.

25. The method of claim 24, further comprising the step of controlling, in response to said measuring step, the drive current applied to the probe so that the probe temperature is substantially equal to the command temperature input.

26. The method of claim 13, wherein the command power input includes an AC command power which is defined by an AC voltage signal having a frequency, $\omega_2$, to heat the sample periodically.

27. The method of claim 26, further comprising the step of substantially linearizing the power response to the command power input by taking the square root of the command power input.

28. The method of claim 26, wherein $\omega_1$ is a high frequency signal, and $\omega_1$ is greater than $\omega_2$.

29. The method of claim 26, further comprising the step of measuring an AC temperature for a load condition and a no-load condition.

30. The method of claim 29, further comprising the steps of subtracting the reciprocal of the no-load AC temperature from the reciprocal of the load AC temperature for at least one of the same DC input temperature point and the same DC input power point of said load and no load conditions, and generating a corresponding output.

31. The method of claim 30, further comprising the step of multiplying the output by said AC command power to determine a complex thermal conductance.

32. The method of claim 13, wherein the command temperature input includes an AC command temperature which is defined by an AC voltage signal having a frequency, $\omega_2$, that provides temperature modulation of the sample.

33. The method of claim 32, wherein $\omega_1$ is a high frequency signal, and $\omega_1$ is greater than $\omega_2$.

34. The method of claim 33, wherein $\omega_1$ is greater than a thermal bandwidth of the probe.

35. The method of claim 34, wherein the thermal bandwidth of the probe is about 1 kHz.

36. The method of claim 32, further comprising the step of determining an amount of power consumed by the probe and generating a corresponding power signal.

37. The method of claim 36, further comprising the step of separating contamination caused by the probe from the power signal.

38. The method of claim 37, wherein said separating step includes performing said determining step for both a load condition and a no-load condition.

39. The method of claim 38, further comprising the steps of subtracting the no-load power signal from the load power signal at the same temperature point and generating a corresponding output signal.

40. The method of claim 39, further comprising the step of dividing the output signal by said AC command temperature to compute a complex thermal conductance.

41. A thermal probe microscope comprising:
an electrically resistive probe having a tip;
a heating current signal that heats the electrically resistive probe a selected amount so as to change a temperature of a sample;
an AC current having a substantially constant amplitude and a frequency, $\omega_1$, wherein said AC current is applied to the electrically resistive probe and does not substantially heat the sample; and
wherein the microscope measures a signal indicative of a tip temperature by measuring a voltage across the electrically resistive probe at frequency $\omega_1$.

42. The thermal probe assembly of claim 41, further comprising a lock-in amplifier for measuring the probe temperature.

43. The thermal probe microscope of claim 41, wherein the probe is a Wollaston wire probe.

44. The thermal probe microscope of claim 41, wherein the amplitude of AC current is constant.

45. The thermal probe microscope of claim 41, further comprising a scanner to appropriately position the probe at a desired location.

46. The thermal probe microscope of claim 41, wherein the probe has a nominal end radius generally less than or equal to 10 μm.

47. The thermal probe microscope of claim 46, wherein the nominal end radius is generally less than or equal to 2.5 μm.

48. The thermal probe microscope of claim 41, further comprising a signal source to manually change at least one of a temperature and a power of the probe.

49. The thermal probe microscope of claim 48, wherein said device is adapted to provide at least one of an AC drive voltage and a DC drive voltage.

50. The thermal probe microscope of claim 49, wherein said AC drive voltage and said DC drive voltage are command temperature inputs.

51. The thermal probe microscope of claim 49, wherein said AC drive voltage is a command power input and said DC drive voltage is a command temperature input.

52. The thermal probe microscope of claim 49, wherein said AC drive voltage and DC drive voltage are command power inputs.

53. The thermal probe microscope of clam 41, further comprising a device that maintains a probe power at a setpoint.

54. The thermal probe microscope of claim 53, wherein said device computes the square root of a command power input.

55. The thermal probe microscope of claim 53, wherein the power setpoint is defined by a command power input to the controller.

56. The thermal probe microscope of claim 55, wherein the command power input includes a DC voltage.

57. The thermal probe microscope of claim 56, wherein the DC voltage is a ramp.

58. The thermal probe microscope of claim 55, further comprising an AC voltage defining a command power input to heat the sample, the AC voltage having a frequency $\omega_2$.

59. The thermal probe microscope of claim 58, further comprising a device to substantially linearize a power response to the command power input.

60. The thermal probe microscope of claim 59, wherein the device comprises square root electronics.

61. The thermal probe microscope of claim 58, further comprising a computer to measure an AC temperature for a load condition and a no-load condition.

62. The thermal probe microscope of claim 61, further comprising an algorithm to subtract the reciprocal of the no-load AC temperature from the reciprocal of the load AC temperature at a DC temperature point or a DC power point to generate an output.

63. The thermal probe microscope of claim 62, further comprising an algorithm to determine a complex thermal conductance by multiplying the output by the applied AC power.

64. The thermal probe microscope of claim 41, further comprising a controller that maintains a probe temperature at a setpoint.

65. The thermal probe microscope of claim 64, wherein the temperature setpoint is defined by a command temperature input to the controller.

66. The thermal probe microscope of claim 65, wherein the command temperature input includes a DC voltage.

67. The thermal probe microscope of claim 66, wherein the DC voltage is a ramp.

68. The thermal probe microscope of claim 65, wherein the command temperature input includes an AC command temperature which is defined by an AC voltage signal having a frequency, $\omega_2$, that modulates the temperature of the sample.

69. The thermal probe microscope of claim 68, wherein $\omega_1$ is a high frequency signal, and $\omega_1$ is greater than $\omega_2$.

70. The thermal probe microscope of claim 68, wherein $\omega_1$ is greater than a thermal bandwidth of the probe.

71. The thermal probe microscope of claim 68, further comprising a computer to determine an amount of power consumed by the probe and to generate a corresponding power signal.

72. The thermal probe microscope of claim 71, wherein the computer separates contamination caused by the probe from the power signal.

73. The thermal probe microscope of claim 72, wherein the computer calculates a corresponding power associated with both a load condition and a no-load condition and generates corresponding power signals.

74. The thermal probe microscope of claim 73, wherein the computer subtracts the no-load power signal from the load power signal for at least one of a DC temperature input point and a DC power input point so as to generate an output.

75. The thermal probe microscope of claim 74, wherein the computer further divides the output by the AC temperature command to measure a complex thermal conductance.

76. A method of operating a thermal probe microscope to measure a parameter associated with a sample, the method comprising:
providing a probe adapted to heat the sample;
applying a measuring current having a frequency $\omega_1$ to the probe;
using both a temperature command input and a power command input to apply a DC heating current and an AC heating current to the probe, the AC heating current having a frequency $\omega_2$ substantially less than frequency $\omega_1$; and
measuring an amplitude of the voltage across the probe at frequency $\omega_1$, the amplitude being indicative of a temperature of the probe, wherein the probe temperature is indicative of the parameter.

77. The method of claim 76, wherein the parameter is a glass transition temperature.

78. The method of claim 76, wherein said measuring step includes using a lock-in amplifier.

79. The method of claim 76, further comprising the steps of measuring a temperature response corresponding to the power command input, and generating a corresponding temperature signal.

80. The method of claim 76, further comprising the step of changing at least one of the probe temperature based on the command temperature input and a probe power based on the command power input.

81. The method of claim 76, further comprising the steps of measuring a power required to heat the probe, and generating a corresponding power signal.

82. The method of claim 81, further comprising the step of substantially eliminating contamination of the power signal by the probe.

83. The thermal probe microscope of claim 76, wherein the probe has a nominal end radius generally less than or equal to 10 μm.

84. The thermal probe microscope of claim 83, wherein the nominal end radius is generally less than or equal to 2.5 μm.

* * * * *